US008260402B2

(12) United States Patent
Ermakov et al.

(10) Patent No.: US 8,260,402 B2
(45) Date of Patent: Sep. 4, 2012

(54) NONINVASIVE MEASUREMENT OF CAROTENOIDS IN BIOLOGICAL TISSUE

(75) Inventors: Igor V. Ermakov, Salt Lake City, UT (US); Werner Gellerman, Salt Lake City, UT (US)

(73) Assignee: Longevity Link, Inc., Salt Lake City, UT (US)

(*) Notice: Subject to any disclaimer, the term of this patent is extended or adjusted under 35 U.S.C. 154(b) by 1111 days.

(21) Appl. No.: 12/134,667

(22) Filed: Jun. 6, 2008

(65) Prior Publication Data
US 2009/0306521 A1  Dec. 10, 2009

(51) Int. Cl.
*A61B 6/00* (2006.01)
*A61B 5/00* (2006.01)

(52) U.S. Cl. ......... 600/476; 600/322; 600/335; 600/473

(58) Field of Classification Search ......................... None
See application file for complete search history.

(56) References Cited

U.S. PATENT DOCUMENTS

| | | | |
|---|---|---|---|
| 5,873,831 A * | 2/1999 | Bernstein et al. | 600/473 |
| 6,167,290 A | 12/2000 | Yang et al. | |
| 6,205,354 B1 | 3/2001 | Gellermann et al. | |
| 6,223,063 B1 | 4/2001 | Chaiken et al. | |
| 6,289,230 B1 | 9/2001 | Chaiken et al. | |
| 7,039,452 B2 * | 5/2006 | McClane et al. | 600/424 |
| 7,558,619 B2 * | 7/2009 | Ferguson et al. | 600/476 |
| 7,593,763 B2 * | 9/2009 | Lambert et al. | 600/476 |
| 2003/0130579 A1 * | 7/2003 | McClane et al. | 600/476 |
| 2004/0254479 A1 * | 12/2004 | Fralick et al. | 600/477 |
| 2005/0197580 A1 * | 9/2005 | Ferguson et al. | 600/476 |
| 2005/0197581 A1 * | 9/2005 | Ferguson et al. | 600/476 |
| 2005/0197582 A1 * | 9/2005 | Ferguson et al. | 600/476 |
| 2007/0078349 A1 * | 4/2007 | Ferguson et al. | 600/476 |
| 2007/0166354 A1 * | 7/2007 | Barrett-Reis | 424/439 |
| 2010/0042001 A1 * | 2/2010 | Ferguson et al. | 600/476 |

OTHER PUBLICATIONS

Ermakov, I.V., M.R. Ermakov, R.W. McClane, and W. Gellermann. "Resonance Raman detection of carotenoid antioxidants in living human tissues." Optics Letters 2001, vol. 26, No. 15, pp. 1179-1181.
Ermakov, I.V., M.R. Ermakov, W. Gellermann. "Noninvasive selective detection of lycopene and β-carotene in human skin using Raman spectroscopy." Journal of Biomedical Optics 2004, vol. 9, No. 2, pp. 332-338.

(Continued)

*Primary Examiner* — Tse Chen
*Assistant Examiner* — Angela M Hoffa
(74) *Attorney, Agent, or Firm* — Gifford, Krass, Sprinkle, Anderson & Citkowski, P.C.

(57) ABSTRACT

A method and apparatus are provided for the determination of carotenoid antioxidants and similar chemical compounds in biological tissue such as living skin. The method and apparatus provide a noninvasive, rapid, accurate, and safe determination of carotenoid levels which in turn can provide diagnostic information of the antioxidant status of tissue. Reflection spectroscopy is used to measure the concentrations of carotenoids and similar substances in tissue. White light is directed upon the area of tissue that is of interest. A small fraction of diffusively scattered light is collected and measured. The tissue is pressured to temporarily squeeze blood out of the measured tissue volume while the reflection spectrum is continuously monitored, displayed, and analyzed in near real time. After an optimal time period of typically 15 seconds, the influence of the dominating hemoglobin and oxyhemoglobin tissue absorptions on the reflection spectra are minimized.

16 Claims, 14 Drawing Sheets

OTHER PUBLICATIONS

Hata, T.R., T.A. Scholz, I.V. Ermakov, R.W. McClane, F. Khachik, W. Gellerman, and L.K. Pershing. "Non-invasive Raman Spectroscopic Detection of Carotenoids in Human Skin." The Journal of Investigative Dermatology 2000, vol. 115, No. 3, pp. 441-448.

The Age-Related Eye Disease Study Research Group. "The Relationship of Dietary Carotenoid and Vitamin A,E, and C Intake With Age-Related Macular Degeneration in a Case-Control Study." Archives of Ophthalmology 2007, vol. 125, No. 9, pp. 1225-1232.

Michaud, D.S., D. Feskanich, E.B. Rimm, G.A. Colditz, F.E. Speizer, W.C. Willett, and E. Giovannucci. "Intake of specific carotenoids and risk of lung cancer in 2 prospective US cohorts." The American Journal of Clinical Nutrition 2000, vol. 72, pp. 990-997.

Kolonel, L.N., J.H. Hankin, A.S. Whittemore, A.H. Wu, R.P. Gallagher, L.R. Wilkens, E.M. John, G.R. Howe, D.M. Dreon, D.W. West, and R.S. Paffenbarger, Jr. "Vegetables, Fruits, Legumes and Prostate Cancer: A Multiethnic Case-Control Study." Cancer Epidemiology, Biomarkers & Prevention 2000, vol. 9, pp. 795-804.

Liu, S., J.E. Manson, I. Lee, S.R. Cole, C.H. Hennekens, W.C. Willett, and J.E. Buring. "Fruit and vegetable intake and risk of cardiovascular disease: the Women's Health Study." The American Journal of Clinical Nutrition 2000, vol. 72, pp. 922-928.

Alaluf, S., U. Heinrich, W. Stahl, H. Tronnier, and S. Wiseman. "Dietary Cartoenoids Contribute to Normal Human Skin Color and UV Photosensitivity." The Journal of Nutrition 2002, vol. 132, pp. 399-403.

Gellermann, W., J.A. Zidichouski, C.R. Smidt, and P.S. Bernstein. "Chapter 6: Raman Detection of Carotenoids in Human Tissue," in *Carotenoids and Retinoids: Molecular Aspects and Health Issues*, eds. L. Packer, U. Obermueller-Jevic, K. Kraemer, H. Sies. American Oil Chemists Society, 2004, pp. 86-114.

Niedorf, F., H. Jungmann, M. Kietzmann. "Noninvasive reflection spectra provide quantitative information about the spatial distribution of skin chromophores." Medical Physics 2005, vol. 32, No. 5, pp. 1297-1307.

Stahl, W., U. Heinrich, H. Jungmann, J. von Laar, M. Schietzel, H. Sies, and H. Tronnier. "Increased Dermal Carotenoid Levels Assessed by Noninvasive Reflection Spectrophotometry Correlate with Serum Levels in Women Ingesting Betatene." The Journal of Nutrition 1998, vol. 128, pp. 903-907.

Stahl, W. U. Heinrich, H. Jungmann, H. Tronnier, and H. Sies. "Carotenoids in Human Skin: Noninvasive Measurement and Identification of Dermal Carotenoids and Carotenol Esters." Methods in Enzymology 2000, vol. 319, pp. 494-502.

\* cited by examiner

1. Reflectivity probe head window applies pressure to skin tissue site.

2. Tissue is squeezed, blood is pushed away from the window's contact area with the skin, blood volume is reduced.

3. Pressured tissue blocks fresh blood supply to the contact area. Remaining blood is loosing oxygen.

4. Tissue with small amount of deoxygenated blood volume (Hb) is ready for spectroscopic reflectivity measurements.

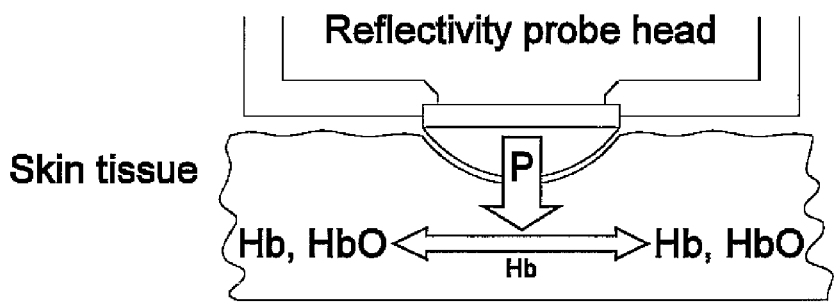

Figure 6

NONINVASIVE MEASUREMENT OF CAROTENOIDS IN BIOLOGICAL TISSUE

FIELD OF THE INVENTION

The present invention relates generally to optical techniques for measuring compounds found in biological tissue. More specifically, the invention relates to a method and apparatus for the noninvasive detection and measurement for levels of carotenoids and related chemical substances in biological tissue, which can be used as a diagnostic aid in assessing antioxidant status and detecting malignancy diseases or risk thereof.

BACKGROUND OF THE INVENTION

High dietary consumption of fruits and vegetables has been associated with protection against various cancers [1, 2] cardiovascular disease [3], and macular degeneration [4]. Furthermore, it is generally regarded as an important factor for increased energy and overall good health. Due to their widespread distributions in fruits and vegetables, carotenoids can be used as an objective biomarker of fruit and vegetable intake, and carotenoids themselves have been speculated to be one of the anticarcinogenic phytochemicals of plant food [1].

The assessment of carotenoid status has often relied upon the collection of plasma or serum samples for high-performance liquid chromatography (HPLC) analysis. While considered to be the current standard, this approach has several important limitations including high cost, fluctuating carotenoid concentrations in blood (relatively short half-lives), and potential selection bias from participants unwilling to agree to venipuncture.

Assessment of carotenoid status from adipose tissue, a more stable repository for lipid-soluble nutrients like carotenoids, has also been considered in some epidemiological studies. However, this method requires biopsies and more complex sample preparation for HPLC analysis. As a result, a need exists for a highly sensitive, non-invasive, and inexpensive method of carotenoid assessment to objectively evaluate fruit and vegetable intake.

The development of optical monitoring technologies has provided an alternative to HPLC for measurements of carotenoids in human living tissues. In particular, resonance Raman spectroscopy, RRS, has been proposed as an objective indicator of carotenoid status [5, 6]. A novel, non-invasive technique used to measure carotenoid status in the skin using light, RRS utilizes a narrow-wavelength light source in the blue wavelength region to measure total carotenoid concentrations in the skin [7]. The Raman scattered light produces a spectral fingerprint of the carotenoid molecules based on their unique molecular structure and their corresponding unique vibrational energy levels [8].

Because carotenoids from fruits and vegetables accumulate in the dermal layer of the skin, RRS can be used to non-invasively detect the concentration of these molecules. The measurements are based on the resonance Raman response originating from the vibrating carbon backbone common to all carotenoids [5]. More specifically, the backbone's carbon-carbon single bond and double bond stretch frequencies each generate a spectrally sharp Raman signal that is shifted from the excitation light frequency by exactly the amount of the respective vibrational stretch frequency. The intensities of the Raman lines are readily isolated from the excitation light via spectrometer or filter, detected with a linear detector array, and quantified.

One of the preferred body sites for Raman scanning has been the palm of the hand because the dermal melanin pigment is lighter and less variable among individuals of different racial and ethnic backgrounds. Additionally, the stratum corneum, the outer dermal tissue layer is relatively thick in the palm (~400 µm). This ensures that the excitation light does not penetrate beyond this strongly scattering layer (light penetration depth ~200 µm) into the deeper tissue layers where it could excite other, potentially confounding chromophores.

RRS used to detect carotenoid levels in the palms of 57 subjects produced a normal distribution [8] with significant width (~50% of the central value). This implies distinct inter-subject variability, an important characteristic of an objective marker of carotenoid status. It has been shown that carotenoid levels measured with RRS in the inner palm of the hand correlate strongly and significantly with HPLC derived carotenoid levels of fasting serum, thus validating the method in an indirect way [9]. Direct validation experiments have recently been completed that involve skin carotenoid Raman measurements followed by biopsy of the measured tissue volume, and subsequent HPLC analysis [10]. Again, a high correlation was found between both methods.

Reflection spectroscopy has been used previously to measure carotenoid macular pigments in the human retina [11]. Compared to the skin, carotenoid levels in the healthy human macula are about two orders of magnitude higher, and the concentrations of potentially confounding chromophores in the retina are relatively low. Furthermore, the optical media of the human eye that are anterior to the retina are relatively transparent, cause significantly less light scattering, and the sclera of the eye can be used as a light reflector that realizes a more or less straight, double-path, propagation of the excitation light through all tissue layers to the sclera and back. These favorable factors make it possible to use a multi-layer sequential light transmission model, in which the individual absorption and/or scattering effects are described with 8-10 respective absorption and/or scattering coefficients, and in which the macular carotenoid pigment levels are derived from a multi-parameter fit of the calculated reflection spectra to the measured spectra.

In human skin, however, the strong light scattering caused by the outer stratum corneum layer does not permit the assumption of tissue light propagation and modeling of straight light paths. Furthermore, there is no effective internal interface that could be used as a reflector. As a consequence, the methodology of [11] is not applicable. While reflection spectroscopy has been used previously for the measurement of skin carotenoid levels [12, 13], these authors did not provide any details about the data derivation, the presented accuracies were relatively low, and no validation of the method was provided. As a consequence, their approach has not been able to find widespread application.

It is thought that the inhomogeneity of tissue chromophore distributions in living human tissue is a major obstacle in the interpretation of noninvasive reflection spectra [14], and that the diffusion theory of light transport is not valid in turbid media. As a consequence, it is thought that tissue inhomogeneities have to be specifically addressed in measurement schemes that limit the source-detector separation to short distances (in the range of ~100 µm), and that require complex spectral deconvolution algorithms involving a multi-compartment light propagation model of tissues.

While human skin reflection spectra have been modeled with high accuracy in the spectral absorption range of hemoglobin and oxyhemoglobin absorptions with this approach, the deconvolution of carotenoid absorptions from spectra measured with this approach has been found to be problematic [14] since the signals are "drowned out" or overwhelmed by other confounding chromophore absorptions. The authors of this approach state explicitly that . . . "the analysis of in-vivo spectra regarding beta-carotene is more sophisticated . . . and will be subject to future examination" [14].

A further attempt to derive skin carotenoid concentrations has explored skin color saturation measurements [15]. In this method, color tri-stimulus b-values are measured, and compared to the chromaticity diagram of a white reflection standard. Since the b-value measures the color saturation from the yellow to the blue region, it can be expected to be influenced by the absorption of skin carotenoids occurring in this spectral range. The measurements are influenced, however, not only by the carotenoid absorption, but also by the superimposed absorption and scattering effects of blood and melanin, thus leading to rather unspecific results.

While RRS is potentially a highly molecule specific and highly applicable, field-usable optical skin carotenoid detection method, care has to be taken that the obtained RRS response is adequately interpreted. Different carotenoid species with differing lengths of the conjugated carbon backbone, such as beta carotene on one hand and lycopene on the other, for example, have slightly shifted spectral absorption bands. RRS detection therefore can favor one carotenoid compound over the other if the excitation light overlaps more with one compound than the other.

Since the relative skin concentrations of beta carotene and lycopene are not known a priori, and since they can differ significantly between individuals [8], the RRS responses may not reflect the true composite carotenoid tissue concentrations if this wavelength dependence is not taken into account. Furthermore, RRS detection of skin carotenoids is an absolute detection technique, meaning that the strength of the RRS carotenoid signal response scales linearly with the excitation light intensity and that it can be artificially decreased if unwanted tissue chromophore absorptions and scattering losses exist in the light path. For these reasons care has to be taken to continually calibrate the RRS measurements against an external carotenoid calibration standard, and to limit the RRS measurements to a skin tissue layer that is free of confounding tissue chromophore absorptions. This is best achieved by limiting the excitation and scattered light beam paths to the outermost layer, the stratum corneum, of the palm of the hand. Potential problems may arise if the light propagation in the external carotenoid calibration standard, which is typically an inorganic material, does not adequately simulate the optical properties of the living tissue.

It would therefore be an advance to provide a method and apparatus for an improved safe, noninvasive, rapid, accurate, and specific measurement of the levels of carotenoids and other similar chemical compounds which are present in varying degrees in biological tissues, and to use this information as a diagnostic aid in assessing antioxidant status and detecting malignancy diseases or risk thereof. Specifically, a method is desirable that is less sensitive to variations in skin carotenoid composition, and that does not require calibration with an external carotenoid standard.

SUMMARY OF THE INVENTION

This invention resides in methods and apparatus for the measurement of carotenoids and other related substances in biological tissue such as living skin. In particular, the method of the present invention provides a noninvasive, rapid, safe, inexpensive, and accurate determination of the levels of carotenoids and similar substances in biological tissue, which in turn can be used as a biomarker for fruit and vegetable intake, and to provide diagnostic information regarding risk of malignancy diseases and risk thereof. Such early diagnostic information allows for the possibility of preventative intervention.

The preferred embodiment uses reflection spectroscopy to quantitatively measure the levels of carotenoids and similar substances in tissue such as skin. In this technique, white light is directed upon the area of tissue of interest, which is pressed against the light delivering probe head. Reflected light from the tissue is measured using a sensitive light detection system, and it is analyzed in terms of its spectral reflection components. Comparing the spectral components of the reflected light with a white reflection standard, the optical density and the directly correlated concentration levels of the skin carotenoid compounds can be quantified non-invasively. The invention is particularly useful in the detection of total carotenoid content in human skin.

These and other objectives and features of the present invention will become more fully apparent from the following description, or may be learned by the practice of the invention as set forth hereinafter.

BRIEF DESCRIPTION OF THE DRAWINGS

In order to illustrate the manner in which the above recited and other advantages and objectives of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting in scope, the invention will be described and explained with additional specificity and detail through the use of the accompanying drawings in which:

FIG. 6 depicts a flow diagram of the events occurring in the measured skin tissue site during the measurement process;

DETAILED DESCRIPTION OF THE INVENTION

Figure 1:
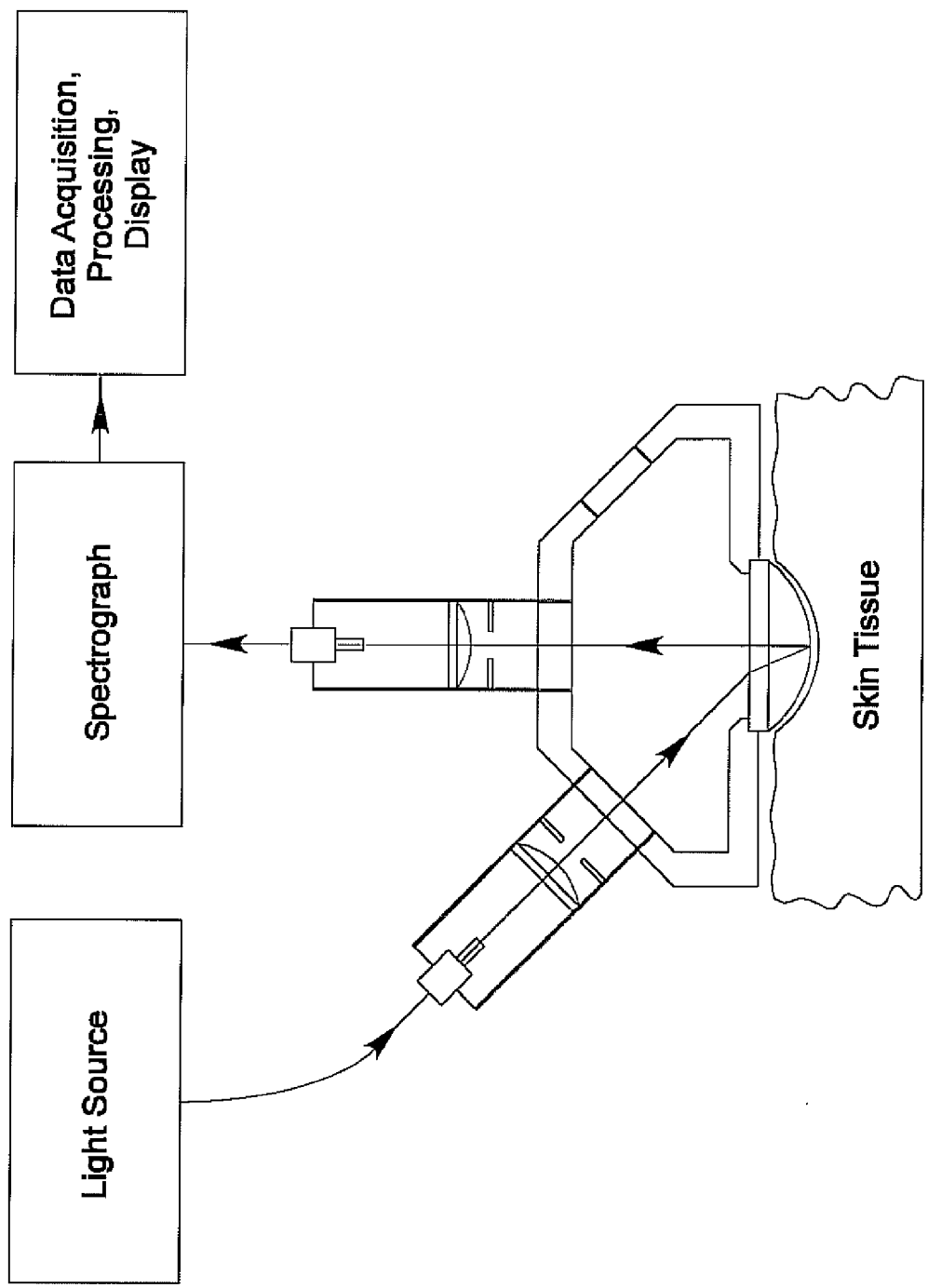
FIG. 1 is a general schematic depiction of the apparatus according to the present invention.

The present invention is directed to a method and apparatus for the noninvasive detection and measurement of carotenoids and related chemical substances in biological tissue. In particular, the present method and apparatus make possible the rapid, noninvasive and quantitative measurement of the concentration of carotenoids, as well as their isomers and metabolites, in biological tissues such as human skin. This is accomplished without the requirement of removing tissue or preparing samples for HPLC analysis, as required by prior "gold standard" techniques.

The invention can be used in a direct and quantitative optical diagnostic technique, which uses low-intensity, white-light illumination of intact tissue, provides for high spatial resolution, and allows for precise quantification of the carotenoid levels in the tissue. Such a technique is useful as a biomarker for fruit and vegetable intake, and it can aid in the detection of tissue abnormalities such as malignancy diseases.

The present invention employs the technique of reflection spectroscopy, which is used to identify and quantify the presence of carotenoids and similar substances in biological tissue such as the skin. In this technique, white light, i.e. light with a large spectral intensity distribution spanning the range from the deep blue to near infrared wavelength region, is directed onto the tissue, and the diffusively scattered light is spectrally dispersed or filtered, and detected. The diffusively scattered light contains spectral regions with diminished light scattering due to the absorption bands of various skin chromophores, including melanin, blood, and all skin carotenoids. The shape and strength of these absorptions can be derived from the reflection spectra, their strength can be quantified in optical density units, and therefore this measure can be used as direct indicator for the concentration levels of the carotenoids present in a subject's skin.

The way the reflection measurements are carried out in this invention help in overcoming the difficulties associated with identifying the carotenoid-specific spectral signatures in the presence of strongly absorbing confounding chromophores. A preferred embodiment uses tissue sites such as the tip of a finger that can be pressed against an optical probe head such that a maximum amount of interfering blood chromophores is squeezed out of the tissue volume to be measured. The apparatus allows one to continuously measure and display the reflection spectra and identify an optimal blood-depleted tissue condition for the eventual recording of a reflectivity spectrum that is useful for the derivation of the tissue carotenoid levels. The total time needed to assess a subject's skin carotenoid levels with the described invention takes about 15 seconds.

In a method for the noninvasive measurement of carotenoids and related chemical substances in biological tissue according to the current invention, a light source such as a 50 W tungsten-halogen lamp is used that features light emission with sufficiently high intensity over a wide spectral range from about 350 nm to upwards of 900 nm. This wide range overlaps the absorption bands of carotenoids in the visible/blue spectral region. When diffusively scattered from the excited tissue volume, the reflected light therefore is influenced by the absorption of the carotenoids and other chromophores present in the measured tissue volume. After squeezing confounding blood chromophores out of the measured tissue volume for a short time, i.e. ~15 seconds, the strength of the composite carotenoid absorption in a subject's skin can be derived. From this strength, in turn, the carotenoid tissue concentration levels are derived, and these can be used to assess the antioxidant status of the tissue. The concentration levels can be compared with levels of normal biological tissue to assess the risk or presence of a malignancy disease.

FIG. 1 is a general schematic depiction of the apparatus of the present invention for measuring carotenoids and like substances in biological tissue using reflection spectroscopy. The apparatus contains a white-light source 100, which in one preferred embodiment is a tungsten-halogen light source. Alternatively, the light source may comprise other devices for generating spectrally broad light. Preferably, in the case of carotenoids, the light source generates light with significant intensities in the wavelength range 350-800 nm, which extends past the absorption range of carotenoids to the deep blue/near UV range and also to the far red/near IR spectral range. Such light is readily available, e.g., from commercially produced inexpensive slide projector lamps. It should be understood, however, that the present invention is not limited to light generated within these wavelengths, since other wavelengths of light could be used if desired, e.g. light from white-light emitting diodes that span the spectral wavelength region past the carotenoid absorption range.

The light source 100 is in optical communication with a light beam delivery (102) and collection (104) system that can include various optical components for directing white light to the tissue to be measured and collecting the diffusively scattered light. As shown in FIG. 1, the optical components of the delivery and collection system include the output port of a fiber bundle 106, a beam expander 108, a collimating lens 109, an aperture 110, a plano-convex lens 112, a second aperture 114, a light collection lens and imaging lens 116, and the entrance port of a second fiber bundle 118. The interaction of these optical components with the light from the light source will be discussed in further detail below.

The light delivery and collection system is in optical communication with a spectrally selective system such as a spectrometer 120, which performs the function of spectrally dispersing the light components of the diffusively scattered light. The spectrally selective system can include various optical components such as diffraction gratings, prisms, holographic filters, dielectric filters, combinations thereof, and the like.

The spectrally selective system is in optical communication with a detection means such as a light detection system 122, which is capable of measuring the intensity of the diffusively scattered light as a function of wavelength in the wavelength range of interest, such as the wavelength range characteristic for the carotenoids in the skin. The light detection system may comprise, but is not limited to, devices such as a CCD (charge-coupled device) detector array, an intensified CCD detector array, a photomultiplier apparatus, photodiodes, or the like.

The spectrally selective system and light detection system can be selected from commercial spectrometer systems such as a low-resolution grating spectrometer employing rapid detection with a charge-coupled silicon detector array. For example, a grating spectrometer can be used which employs a dispersion grating with 300 lines/mm, and a silicon detector array with 14 μm individual pixel width. Another suitable spectrometer is a holographic imaging spectrometer, which is interfaced with a CCD detector array an employs a volume holographic transmission grating. The spectrally selective system and light detection system can also be combined into an imaging system that includes spectrally selective optical elements used in association with a low light level CCD imaging array such as an intensified CCD camera.

The detected light is preferably converted by a light detection system into a signal that which can be visually displayed on an output display such as a computer monitor or the like. It should be understood that the light detection system may also convert the light signal into other digital or numerical formats, if desired. The resulting diffusely scattered light signals are preferably analyzed via a quantifying means such as a quantifying system, which may be calibrated by comparison with chemically measured carotenoid levels from other experiments. The quantifying system may be a computer, preferably one in which data acquisition software is installed that is capable of spectral manipulations, such as the normalization of the spectra to a diffusively scattering white reference standard, and the determination of optical density values for the carotenoids present in the measure tissue volume. The quantifying system may also comprise a CCD image display or monitor. The quantifying system may be combined with the output display in one computer and can calibrate the results with carotenoid levels obtained with other experiments such as the optical density that is proportional to actual carotenoid levels.

During operation of the apparatus, a light beam is generated from the light source and is directed through an input optical fiber to delivery and light collection system. The expanding light beam is collimated and directed to a lens that is in physical contact with the tissue to be measured. The diffusively scattered light from the tissue is then collected by a second lens and imaged onto the face of an output fiber bundle that routes the light to a spectrally selective system such as a grating spectrograph. The spectrally dispersed light is directed to a light detection system that measures the light intensity as a function of wavelength in the wavelength range spanning across the absorption bands of all skin chromophors. The light detection system then converts the diffusively scattered light signals into a form suitable for visual display such as on a computer monitor or the like, and the resulting carotenoid absorption is analyzed with the quantification system.

The present invention is particularly useful in the detection of total carotenoid content in human skin. As discussed in issued U.S. Pat. No. 6,205,354, the entire content of which is incorporated herein by reference, several of the carotenoids which have been found to be associated with healthy skin include all-trans-β-carotene, lycopene-α-carotene, γ-carotene, phytoene, phytofluene, septapreno-β-carotene, 7,7'-dihydro-β-carotene, astaxanthin, canthaxanthin, zeaxanthin, lutein, β-apo-8'-carotenal, violaxanthin, and rhodoxanthin. These are chain-like molecules with different lengths and attachments, all having a carbon backbone with alternating carbon double and single bonds, respectively. The vibration of these bonds, common to all carotenoids, can be detected with Raman spectroscopy. It is known from separate measurements that the wavenumber shifts of these carotenoids are generally in the range from 800 to 2000 $cm^{-1}$ (wavenumbers). For example, the carotenoids lutein and zeaxanthin are known to have wavenumber shifts of approximately 1160 $cm^{-1}$ and 1520 $cm^{-1}$, respectively.

Carotenoids are an important component of the skin's antioxidant defense systems, where they are thought to act as free radical and singlet oxygen scavengers. Furthermore, carotenoids protect the skin from a number of harmful reactive oxygen species (ROS), which are formed, for example, by excessive exposure of skin to ultra-violet (UV) light such as from sunlight. The ROS can potentially cause oxidative cell damage and the formation of skin cancers such as basal cell carcinoma, squamous cell carcinoma, and malignant melanoma. In addition, UV light exposure can lead to immunosuppression and premature skin aging. Once formed, the ROS efficiently react with DNA, proteins, and unsaturated fatty acids, causing DNA strand breaks and oxidative damage, as well as protein-protein and protein-DNA cross links. Oxidation of lipids can result in the formation of lipid peroxides which persist a relatively long time in the cells and can thus initiate radical chain reactions and enhance oxidation damage.

It has been previously demonstrated that there is a correlation between the levels of carotenoids, retinoids, and similar chemical substances in the skin and the risk of skin cancer and other skin disorders. People with low levels of carotenoids in their skin are at a significantly greater risk of getting skin cancer. Therefore, if a determination can be made of the levels of carotenoids which are present in the skin, the risk for cancer can be assessed; and if low levels of carotenoids are measured, preventative steps can be taken, such as dietary supplements.

Current methods for evaluating the presence of skin cancer generally include excising an area of the suspected tissue and performing a histological analysis. This is an invasive procedure and is usually performed in the later stage of cancer, and thus is not useful in early detection of cancer or precancerous conditions in an efficient and timely manner in order to provide proper treatment. The present invention overcomes these difficulties by providing for early noninvasive measurement of carotenoids to aid in the determination of cancer risk.

The present invention not only provides for a rapid, non-invasive assessment of carotenoid levels in a variety of human tissues and bodily fluids, but also has many additional beneficial uses. These include assessing the overall antioxidant status in human tissue; providing for early cancer detection using spatially resolved reflection data or reflection images; providing a screening tool suitable for use in large population studies of cancer prevention and other diseases involving carotenoids or other antioxidants; providing for monitoring of dietary manipulation of tissue carotenoid or other antioxidant content; and providing a tool to assess carotenoid distribution and uptake from cosmetic compounds.

The methods and apparatus of the invention are especially effective in measuring the carotenoid levels in skin, skin lesions, and skin malignancies. The present invention allows two-dimensional reflection mapping to be developed which will provide a non-invasive method for defining tumor margins, thus eliminating time consuming and tedious sections and allowing for instant intraoperative tumor margin delineation. The measurement of carotenoid levels can also be used as a predictor of malignant potential of individual cutaneous lesions.

Various experiments were performed which demonstrate that strong reflection signals are readily obtainable for various areas of living human skin using low light exposures. The following examples set forth the apparatus and procedures utilized in these experiments as well as the results derived therefrom.

EXAMPLE 1

Figure 2:
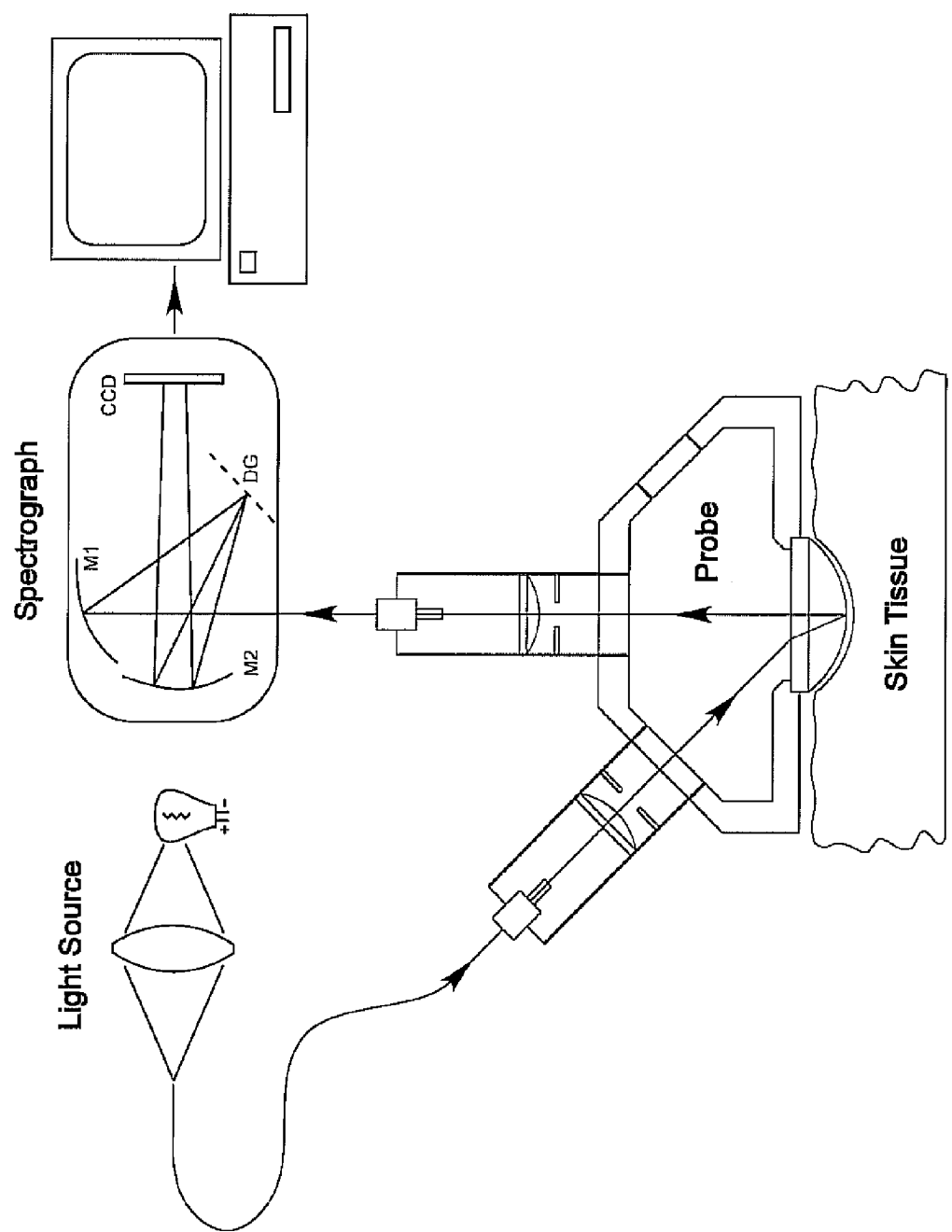
FIG. 2 is a schematic depiction of an experimental apparatus according to the present invention.

An experimental apparatus suitable for reflection-based measurements of carotenoids in human skin is schematically shown in FIG. 2. The apparatus includes a probe head module 202 which contains the light beam delivery and collection system, a light source and detection module 204 that contains a light source and a light dispersion, detection, and analyzer system, and a computer 210 for data acquisition, processing, and display. The light module is designed as a hand-held beam delivery and collection device with a lens that can be brought in direct contact with the diffusively scattering skin tissue site (e.g. a finger of the hand) and that allows the tissue to be pressed against the lens.

As excitation source, the light output of a BRL 50 W tungsten halogen lamp (Ushio, Inc.) is used. The light is in optical communication with the probe module such that the excitation light is routed through an optical multimode fiber into the probe module during operation. The light source is operated with a current-stabilized power supply that limits current fluctuations to less than 1%. A lens/reflector combination serves to couple the lamp output into an identical optical fiber.

Both fibers have a core diameter of 500 μm. At the output end of the fiber inside the optical probe head module, a high-refraction plano-convex lens collimates the light and directs it towards a lens that can be brought into direct contact with the skin tissue site. An aperture is used to limit the excitation beam diameter to 3 mm. The diffusively scattered light is collimated in a geometry that is off from the exact backscattering direction by 45 degrees. This geometry minimizes the propagation of spectrally reflected light into the detection system.

The diffusively reflected light components are apertured, imaged by a lens onto an optical fiber, and routed into a spectrograph for spectral dispersion and corresponding spectrally selective detection of the reflected light with a linear CCD detector array. The CCD array is operatively connected with a personal computer such that the signals detected on the detector array are displayed on a monitor of the computer.

Prior to any skin measurements, a dark spectrum $D(\lambda)$ is recorded that provides a background signal intensity for each pixel of the detector array, this taking into account any hot pixels of the array, and any minor light scattering inside the optical probe and the spectrograph. As a next step, a diffuse reflection spectrum is measured from a "white" reflection reference standard ("Spectralon", Lab Sphere, Inc.), and stored in the computer memory. For the measurement of skin carotenoid levels, the tissue site of interest is pressed against the lens. This squeezes blood out of the measured tissue volume, depletes the oxygen content of the small fraction of blood remaining in the volume, and also blocks the re-supply of fresh, oxygen-rich blood. As a result, the influence of blood chromophore absorptions to the skin reflection spectrum is drastically reduced in the squeezed tissue volume, and thus the optical properties of the skin are optimized for a reflection-based measurement of skin carotenoids, as further described below.

The reflectivity spectrum $R(\lambda)$ is calculated according to the expression $$R(\lambda) = \frac{T(\lambda) - D(\lambda)}{S(\lambda) - D(\lambda)} \cdot 100\%$$

where $T(\lambda)$ and $S(\lambda)$ are the signals measured at wavelength $\lambda$ from the skin tissue and reflectivity standard, respectively, and $D(\lambda)$ is the signal at any wavelength $\lambda$ due to the dark spectrum intensity.

Data processing converts the normalized reflectivity spectrum $R(\lambda)$ into an "apparent" optical density spectrum $A(\lambda)$ by talking the decimal logarithm for each spectral data point of the reflectivity spectrum, according to the relation $$A(\lambda) = -lg\left(\frac{R(\lambda)}{100}\right)$$

Various mathematical routines, described in more detail in the following sections, are possible to extract the spectral contributions and absolute concentration levels of skin carotenoids from the recorded spectra.

EXAMPLE 2

Figure 3:
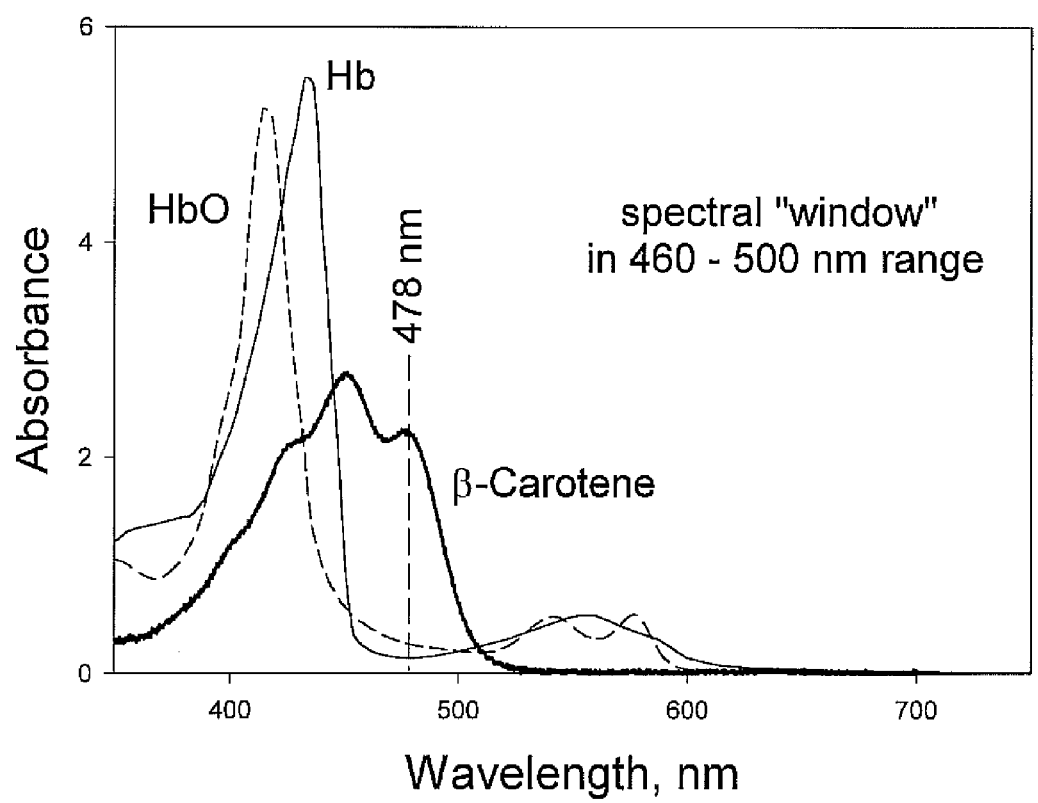
FIG. 3 shows model absorption spectra of the three main absorbers in human skin tissue.

To set the absorption properties of the various chromophores encountered in skin into perspective, model absorption spectra are shown in FIG. 3. The three main absorbers in living human skin tissue are oxygenated hemoglobin, HbO (dashed line), deoxygenated hemoglobin, Hb (solid thin line), and carotenoids (shown as an example for beta-carotene as solid fat line). Strong interference of HbO and Hb with the carotenoid absorption exists in the 350-460 nm region, while a spectral window of reduced interference exists in the 460-500 nm range. The magnitude of the interference, of course, depends strongly on the concentration of the blood chromophores present in the measured tissue volume, and can be so high that it overwhelms the skin carotenoid absorption. The pressure technique used in the reflectivity measurements leads to a strongly increased contrast between carotenoid absorption and the absorption background caused by HbO and Hb. Furthermore, by converting HbO into Hb while blocking the supply of the measured tissue volume with fresh blood, HbO, the absorption contrast in the carotenoid range at 480 nm is additionally increased by at least twice a factor of two.

EXAMPLE 3

The index finger of the left hand was pressed against the lens of the apparatus of FIG. 2 for 15 seconds while the tissue area in contact with the lens was illuminated with the white excitation light. Immediately after pressing the finger onto the reflectivity probe head lens, reflection spectra are acquired, processed, and monitored in near real-time on the computer monitor (proving an updated spectrum every second. This allows one to monitor gradual changes in the reflectivity spectrum caused by the changing HbO/Hb balance in the measured tissue volume.

Figure 4:
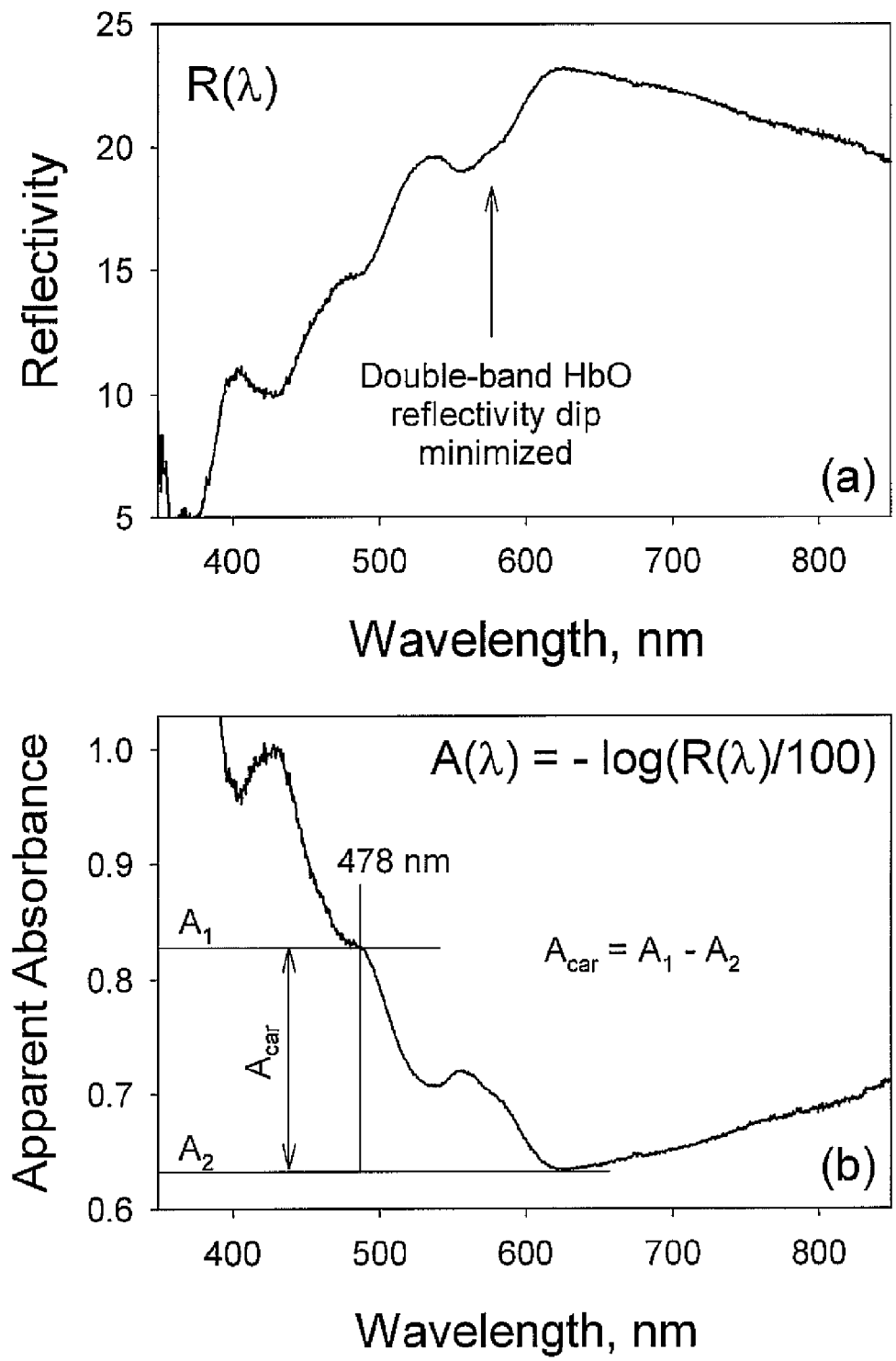
FIG. 4 shows a reflectivity spectrum and derived absorbance spectrum of a skin tissue site that is pressed against the optical probe head of the apparatus, and that illustrates a simplified data analysis procedure for the determination of skin carotenoid levels.

Specifically, one sees the gradual disappearance of the double-band HbO feature in the 500-600 nm range, and therefore one is able to determine the best time to record an optimal reflectivity spectrum for the derivation of skin carotenoid levels. An optimal reflection spectrum obtained in this way for the index finger of the left hand of a healthy volunteer subjects is shown in FIG. 4. The data are plotted as percent reflectivity according to expression (2) shown above.

The bottom plot in FIG. 4 shows the absorbance spectrum derived by the computer software from the reflectivity spectrum shown at the top of FIG. 4, using the relation (1) shown above. The apparent optical density of the skin carotenoids in the skin tissue site is chosen as the difference between the total apparent absorbance value at 478 nm and the absorbance due to the combined scattering/absorption background due to all remaining chromophores (residual Hb, HbO, and melanin). The calculation of the background absorbance level can be carried out in several ways. Our correlation/validation experiments described in more detail below show that the apparent absorbance level of human skin at 479 nm can be well approximated with the absorbance level at around 620 nm, where the contribution of blood components is negligible. The rationale for the choice of 620 nm as the background wavelength is further based on the fact that the scattering properties of the skin do not change significantly from 480 to 620 nm. The carotenoid optical density value derived for the skin tissue in this case is A(480)−A(620)=0.83−0.63=0.2 optical density units.

EXAMPLE 4

Figure 5:
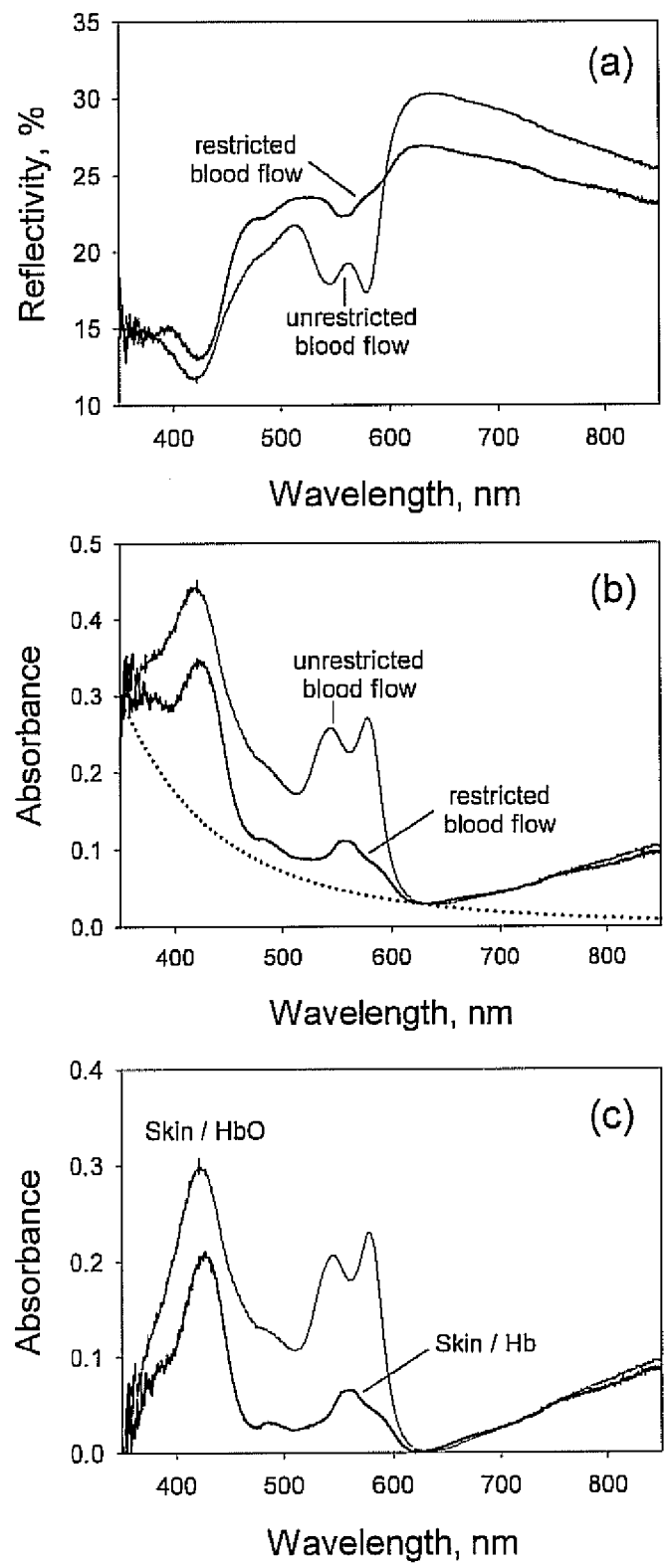
FIG. 5 shows reflection and derived absorption spectra of living skin tissue without restricted blood flow and restricted blood flow, respectively.

The influence of arterial blood flow restriction on measured in-vivo skin reflectivity spectra, and the corresponding reflectivity-derived, "apparent absorbance" spectra, measurements were further investigated and the results are illustrated in FIG. 5. Panels (a) and (b) show the reflectivity and corresponding absorbance spectra, respectively, for the case of unrestricted blood flow to the measured issue site, and for the case after blood flow to the same tissue site had been restricted. Panel (c) shows the apparent absorbances for unrestricted and restricted blood flow after background subtraction.

Restriction of blood flow was realized with the help of an inflatable arm cuff of a conventional blood pressure meter, positioned above the elbow of the left arm of a volunteer subject, and pressurized to 200 mm Hg. The restricted blood flow spectrum was measured after applying the pressure cuff for about 2 minutes. As shown in the spectra obtained before and after blood flow restriction, drastic spectral reflectivity and corresponding absorption changes occur at almost all wavelengths of the measured spectral range.

As can be seen from the results displayed in FIG. 5, the characteristic pronounced double-band spectral feature of oxygen-reach blood (HbO) in the reflectivity spectrum in the 540-590 nm range nearly disappears while a weaker, single-band component of oxygen-less blood (Hb) appears in the spectral range around 570 nm after blood flow restriction. Furthermore, a significant reduction in absorption occurs in the spectral range of the skin carotenoid absorption region near 480 nm. Importantly, the small absorption band feature at 480 nm, which is due to the longest wavelength vibronic transition peak of carotenoids, becomes significantly more pronounced with respect to the absorption background of other species after blood flow restriction (FIG. 5c).

In order to derive the carotenoid absorption strength quantitatively from the measured reflectivity spectra, the scattering background in the reflectivity spectrum in the 350-700 nm wavelength range is approximated with a 1/lambda^n wavelength dependence (dotted curve in FIG. 5b). The scattering background is anchored at two wavelength positions of the reflectivity spectrum where any absorption contributions from blood can be expected to be absent, or at least be minimal, and where no reflectivity changes are seen upon blood flow restriction. The long wavelength point is at about 620 nm, and the short wavelength point is about 350 nm.

EXAMPLE 5

The functioning of the optical light delivery and collection module (reflectivity probe head) is illustrated as a flow diagram for events occurring in the skin in FIG. 6. The in-vivo reflectivity measurement starts by pressing the skin tissue site to be measured, typically the palm of the hand or the tip of a finger, against the convex lens window of the probe head. This compresses the tissue volume, with more pressure applied in the central area as compared to the peripheral area. As a consequence, blood is squeezed out of the tissue, thus reducing the effective blood (Hb) volume. Additionally, the supply of fresh, oxygenated blood (HbO) is blocked. This leads to a quick decrease of the oxygen concentration in the remaining blood volume. As a result of these two events, the tissue site is optimally prepared for the reflectivity-based determination of skin carotenoids, since the spectral contributions from Hb and HbO are drastically reduced in the wavelength range critical for the measurement.

EXAMPLE 6

Figure 7:
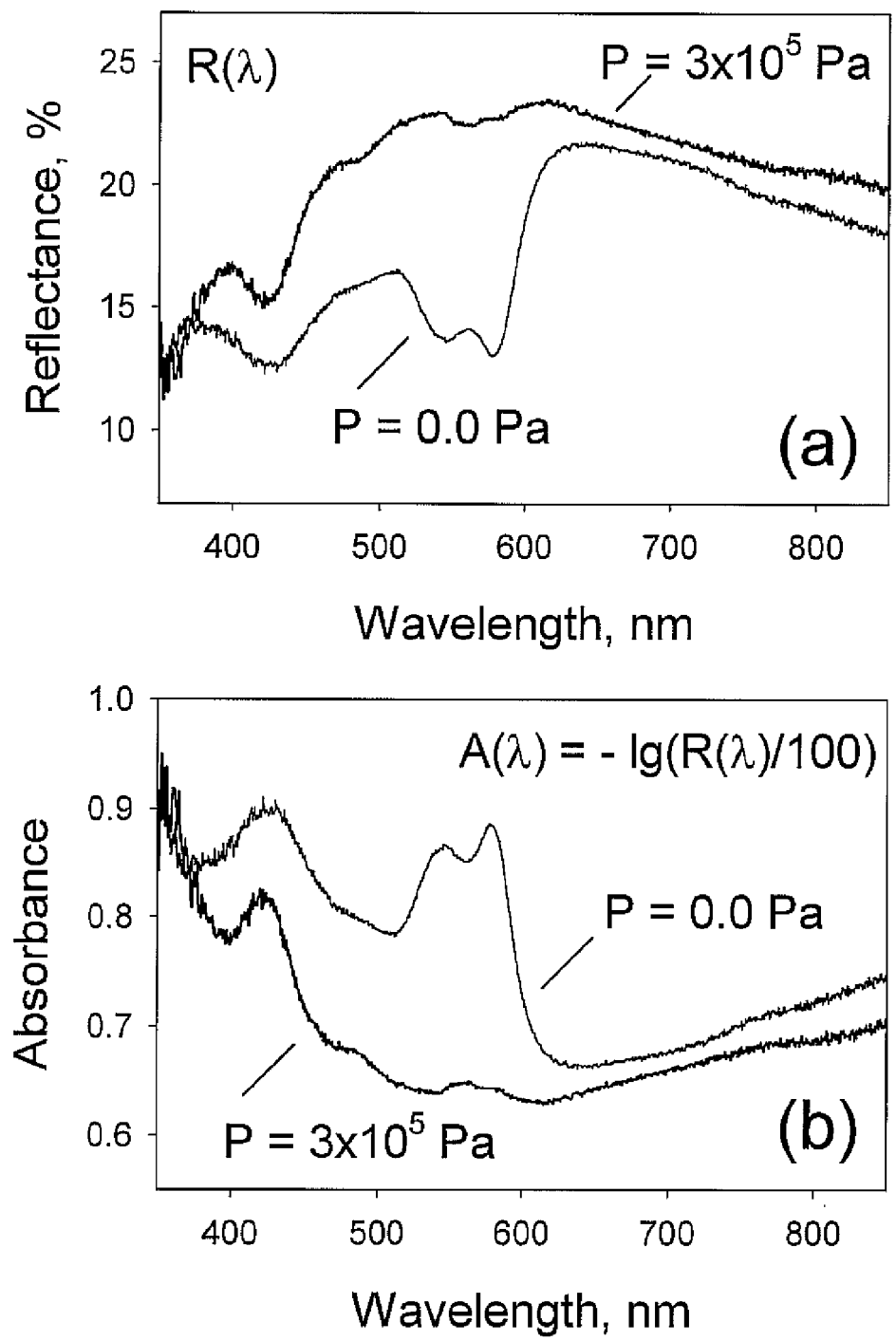
FIG. 7 shows reflectivity spectra and derived absorption spectra of a human skin tissue site that is pressed against the optical probe head of the apparatus.

To illustrate the optical clearing effect in tissue sites pressed against the probe module lens, diffuse reflection measurements were carried out for the index finger of a healthy volunteer subject. The results for the reflectivity spectra and corresponding derived absorption spectra are shown in FIG. 7 and are compared with the corresponding spectra for the case where the finger is only in gentle contact with the lens. The pressure exerted on the finger when pressed against the window was estimated as ~3 atm. As is evident from panel (a), a strong optical "clearing" effect is achieved in the tissue site since the spectral components of HbO and Hb are almost completely eliminated in the visible spectral region. This renders the spectral range of the carotenoid absorption band near 480 nm nearly free of interfering blood absorptions.

Figure 8:
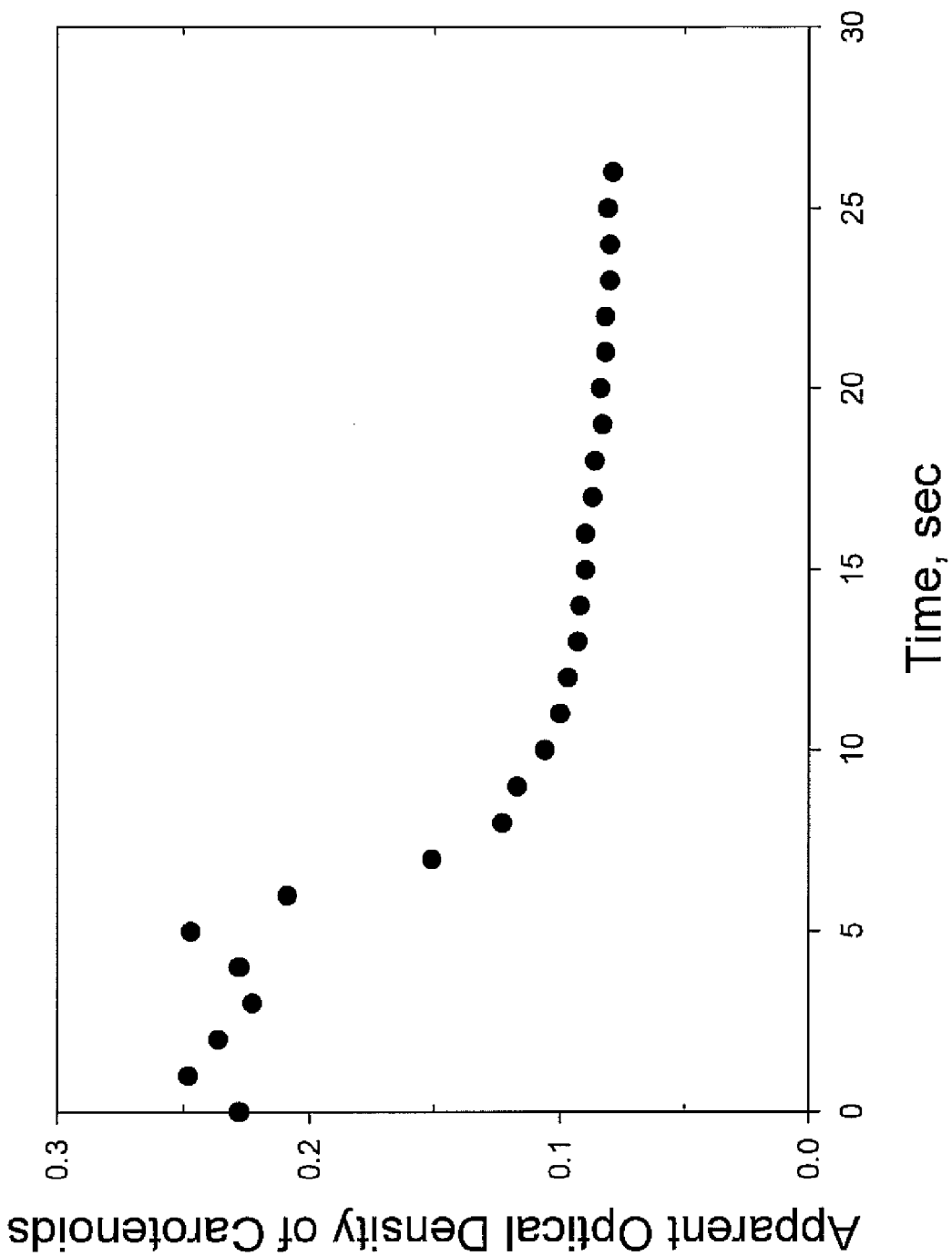
FIG. 8 shows the apparent optical density of skin carotenoids derived from the reflectivity measurements versus time, while pressing the measured tissue volume against the probe head lens.

To further illustrate this tissue "clearing" effect quantitatively, the apparent optical density of skin carotenoids was measured for a volunteer subject at several dozen discrete time points after the subject's finger was pressed against the probe head lens. The results are shown in FIG. 8. For the first 4 seconds, the finger was in only gentle contact with the probe head window and therefore no pressure was applied. In this tissue condition an artifactually high apparent optical density is derived from the reflectivity measurements.

When starting to press the finger against the probe head lens, the derived optical density values decrease quickly, within a few seconds, by a factor of ~2.5, and then further decrease gradually to a steady-state level after about 10 seconds. It takes this roughly 10 second time period until the interfering blood chromophores are squeezed out of the pressured blood volume that is measured and consequently, until the final reflection measurement should be recorded that is used for a meaningful derivation of skin carotenoid levels.

EXAMPLE 7

Figure 9:
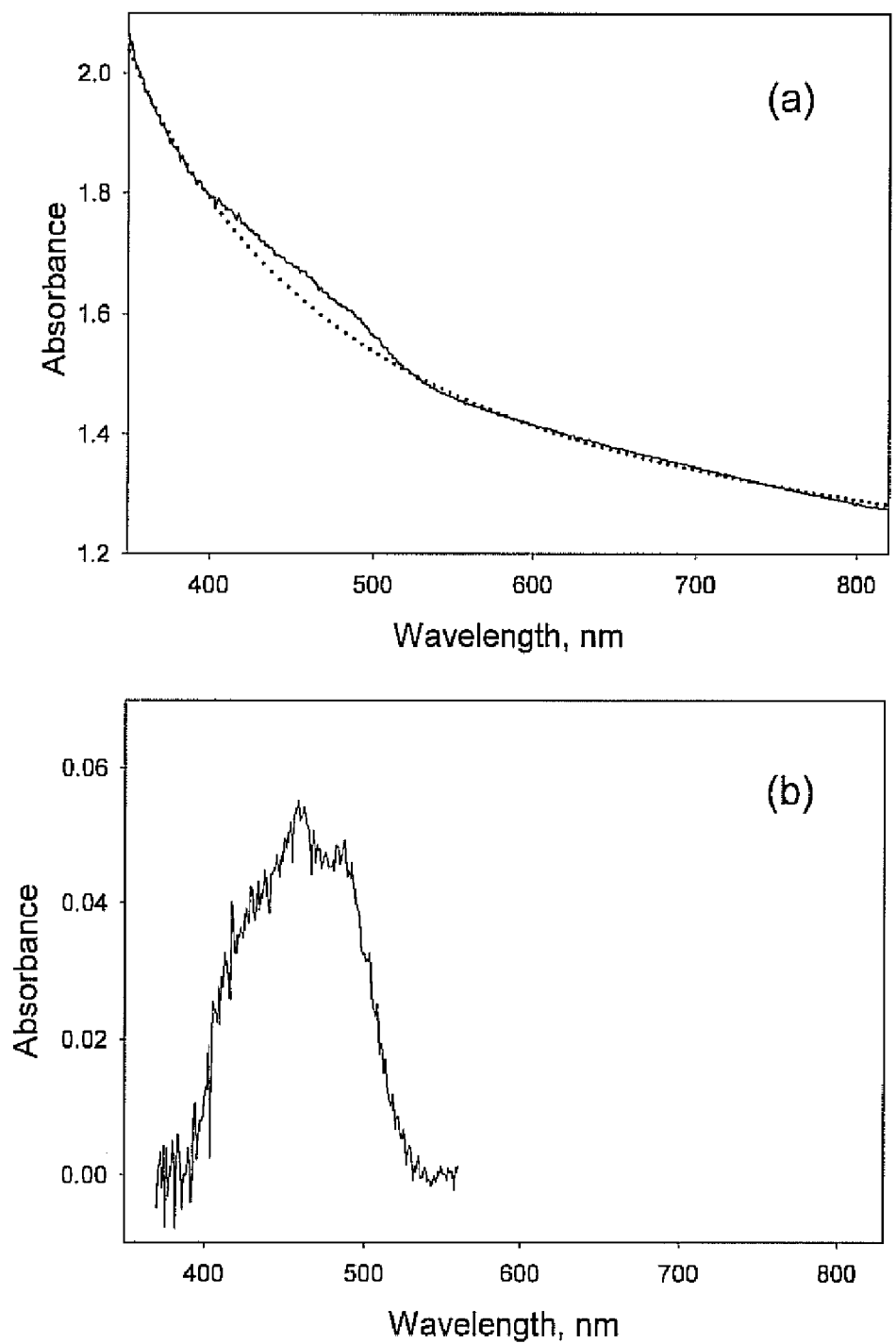
FIG. 9 shows an absorbance spectrum of an excised, bloodless heel tissue sample in the 350-800 nm wavelength region, the underlying scattering, and the derived skin carotenoid absorbance spectrum.

To validate the reflectivity method of the invention, the skin carotenoid absorption was measured directly for a thin excised tissue sample with a transmission spectrometer, and the result compared with the carotenoid absorption determined for the same sample with the reflection method. For the absorption measurement, a ~0.7 mm thick tissue sample was removed from the heel of a foot of a volunteer subject, sandwiched between two thin glass cover plates, and measured in the 300-800 nm wavelength range with an absorption spectrometer. The spectrum, shown in panel (a) of FIG. 9, reveal a carotenoid absorption in the 400-500 nm wavelength range superimposed on a scattering background that monotonously increases from the long to short wavelength regions. The dotted line in the absorption spectrum marks the simulated scattering background in the carotenoid absorption region. After subtraction of the background from the measured spectrum, the absorption spectrum shown in panel (b) is obtained, clearly revealing the three distinct vibronic absorption features characteristic of carotenoid absorption bands.

Figure 10:
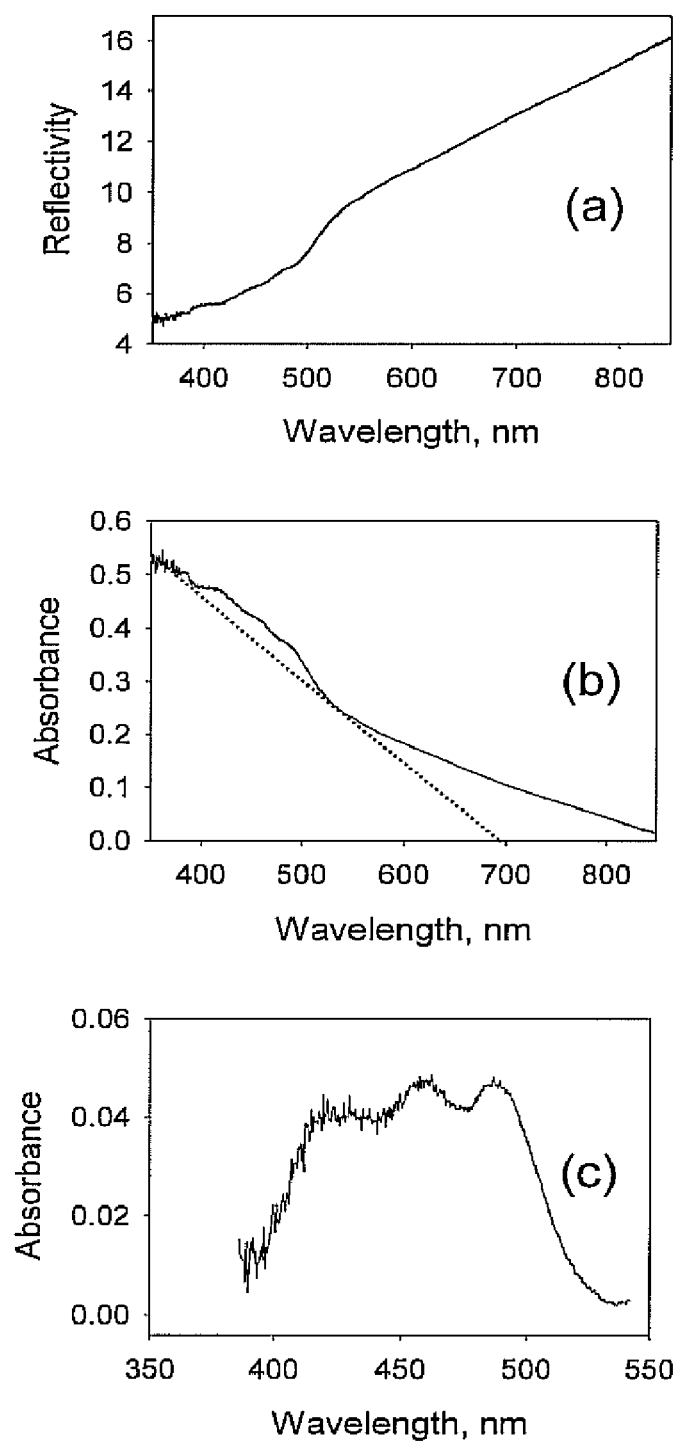
FIG. 10 shows reflectivity and apparent absorbance spectra for an excised, bloodless heel tissue sample, obtained via reflection measurements, and the resulting absorbance spectrum of skin carotenoids derived from these measurements.

Following the absorption measurements the excised sample was measured with the reflection apparatus shown in FIG. 2. The results are shown in FIG. 10. Panel (a) shows the normalized reflectivity spectrum over the wavelength range 380-850 nm. The skin reflectivity increases gradually from short to long wavelengths, with an apparent dip in the carotenoid absorption range (400-520 nm range). Panel (b) shows the absorbance spectrum derived from the reflectivity spectrum (a) via relation A=−lg (R/100) for each spectral data point. The dotted line approximates the scattering background in the carotenoid absorption range. Panel (c) shows the carotenoid absorbance spectrum derived from absorbance spectrum (b) after subtraction of the scattering background in spectral range 380-540 nm.

Figure 11:
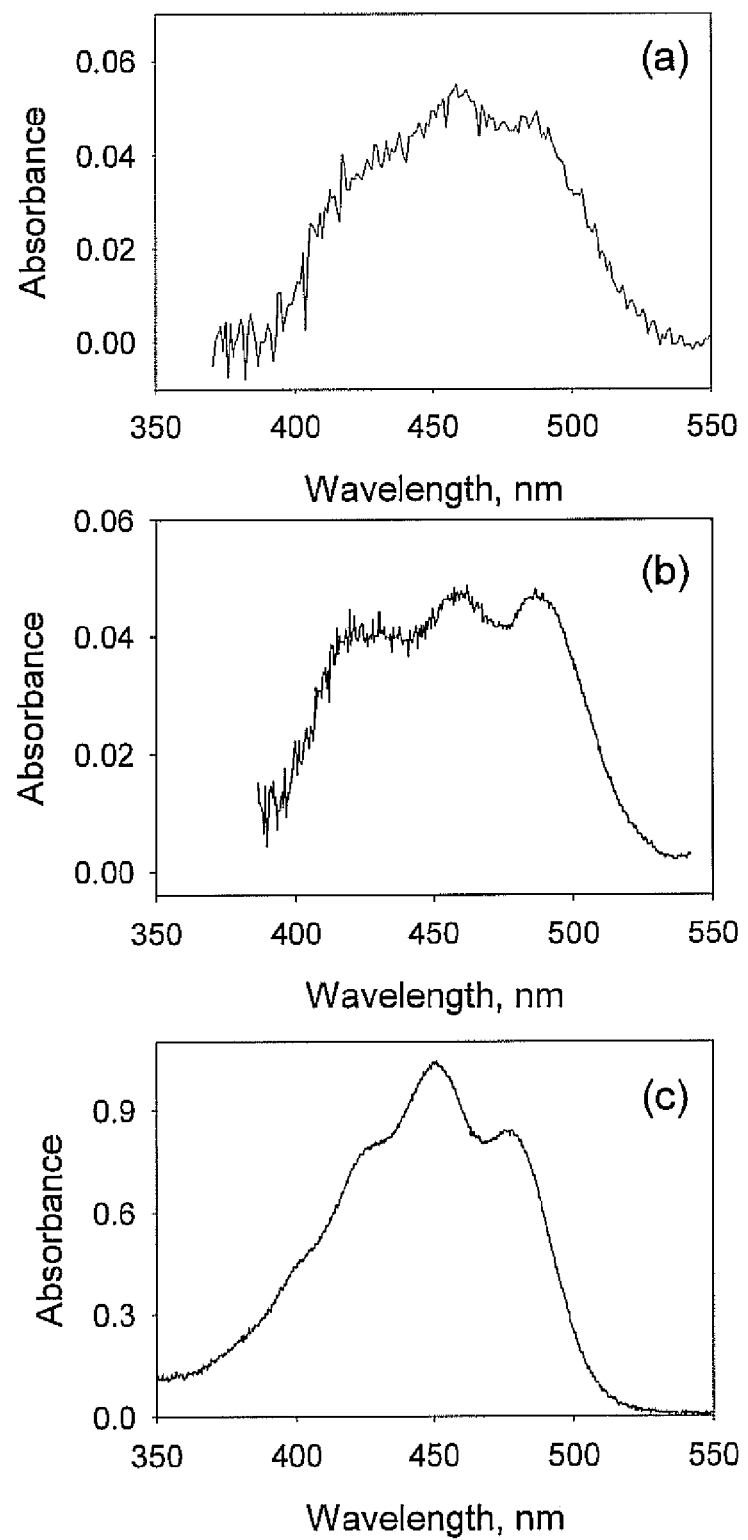
FIG. 11 shows carotenoid absorbance spectra obtained for an excised, bloodless heel tissue sample via transmission and reflectivity measurements, and compares these spectra with the absorbance spectrum of a beta carotene solution.

The absorption spectra obtained for the excised heel tissue sample via direct transmission measurement, and the absorbance derived from the reflection measurement are plotted in FIG. 11 in the same wavelength scale and are compared with the absorption spectrum of β-carotene solution in methanol. A close resemblance of the skin carotenoid spectra with the absorbance spectrum of the pure carotenoid solution is apparent, again, including the spectral position, halfwidth, and vibronic substructure. Also, the peak absorbance levels of the tissue sample measured with transmission and reflection technique are identical. Small differences in the shape of the carotenoid skin spectrum compared to the spectrum from a pure beta carotene solution is due to the more complex carotenoid composition of human skin, which contains additional carotenoid species besides beta carotene with slightly different absorption profiles.

EXAMPLE 8

Figure 12:
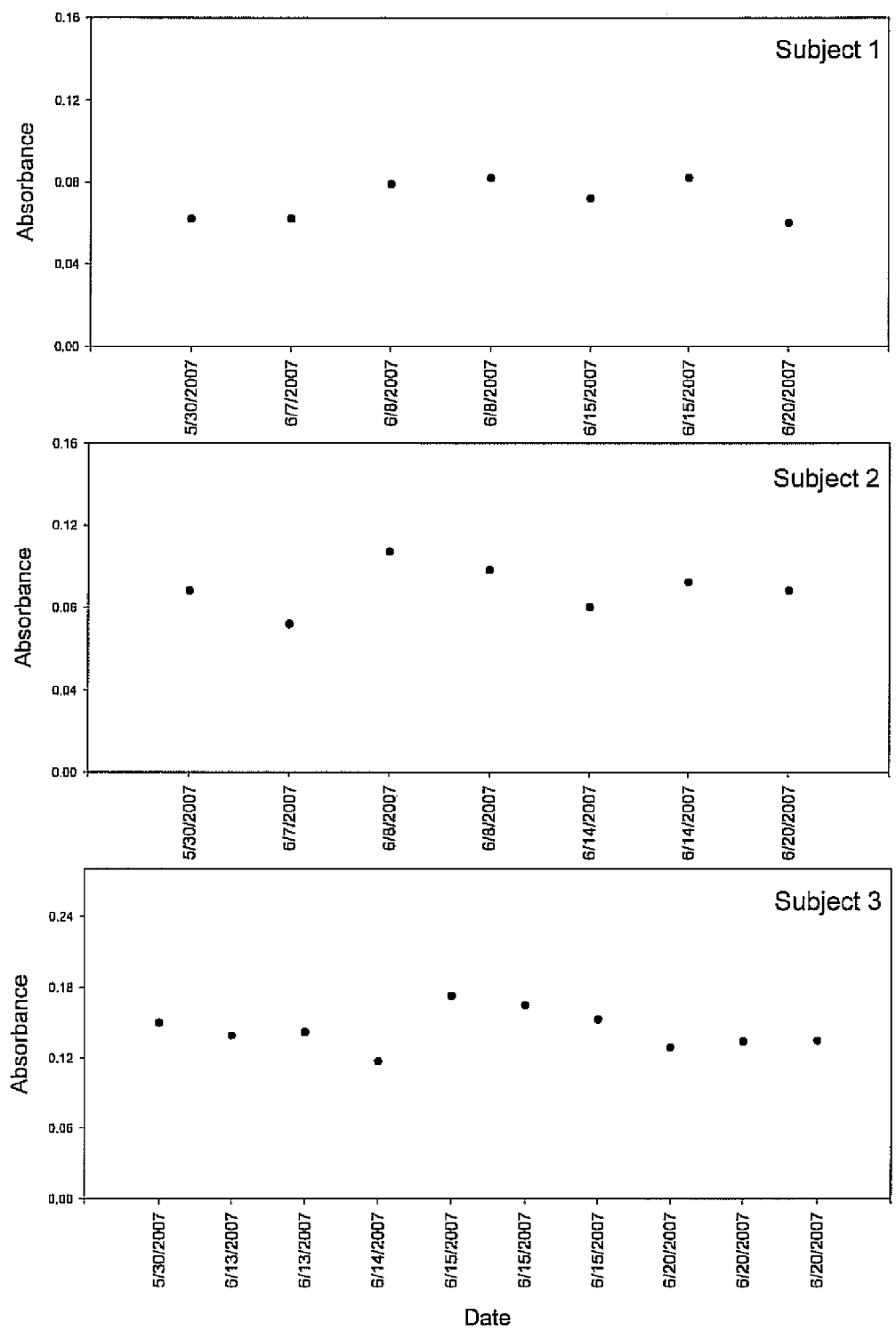
FIG. 12 shows the short- and long-term reproducibility of reflectivity-based skin carotenoid measurements.

The reproducibility of reflectivity-based skin carotenoid measurements was measured for three volunteer subjects. Carotenoid levels in the palm of the subjects were measured repeatedly over a time span of several days and weeks. The results from the absorbance levels are shown in FIG. 12. Each data point represents an average of 3 consecutive measurements. Good short and long-term reproducibility of carotenoid levels are observed in all cases.

EXAMPLE 9

Figure 13:
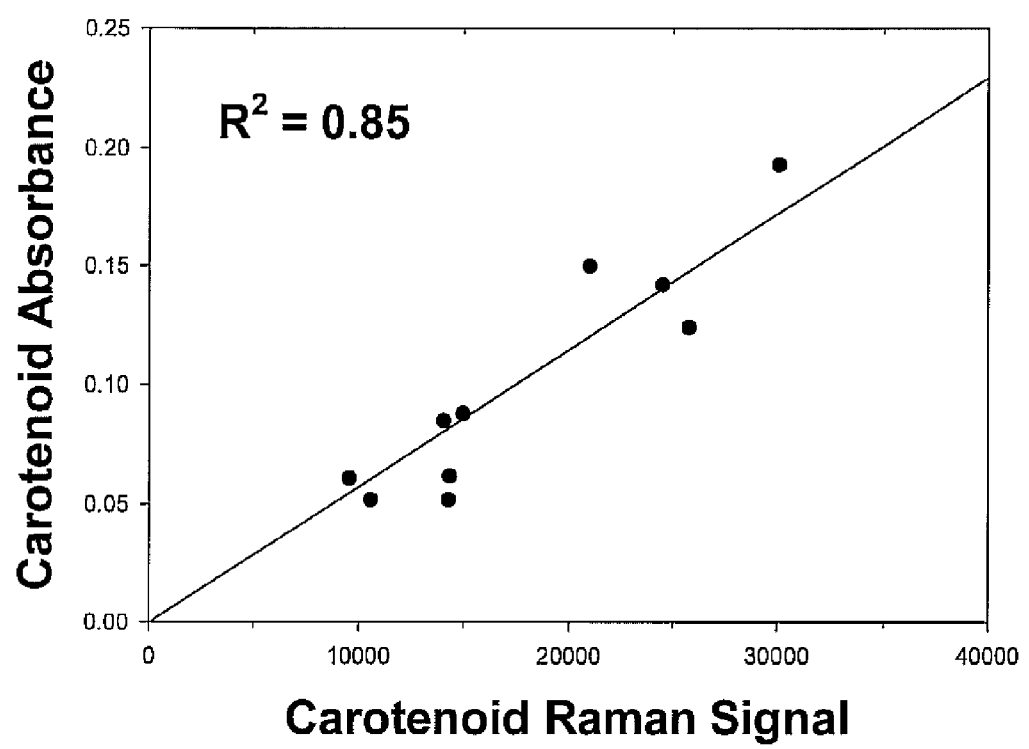
FIG. 13 shows a correlation of skin carotenoid levels determined with Raman spectroscopy and reflection spectroscopy, respectively.

FIG. 13 shows the correlation between two independent, completely different, optical methods used to measure carotenoid levels in the palm of 10 volunteer subjects. One method is the reflectivity method described in this patent application, and the other one is the previously patented method of Resonance Raman spectroscopy. Carotenoid absorbance levels determined from reflectivity measurements are plotted for each subject versus the strength of the carbon-carbon double bond carotenoid Raman response measured with the Resonance Raman method. A high correlation with a squared correlation coefficient of $R^2$=0.85 is obtained. The high correlation level serves as validation of the proposed reflectivity-based carotenoid measurements technique and justifies the background selection procedure described above (FIG. 4).

EXAMPLE 10

Figure 14:
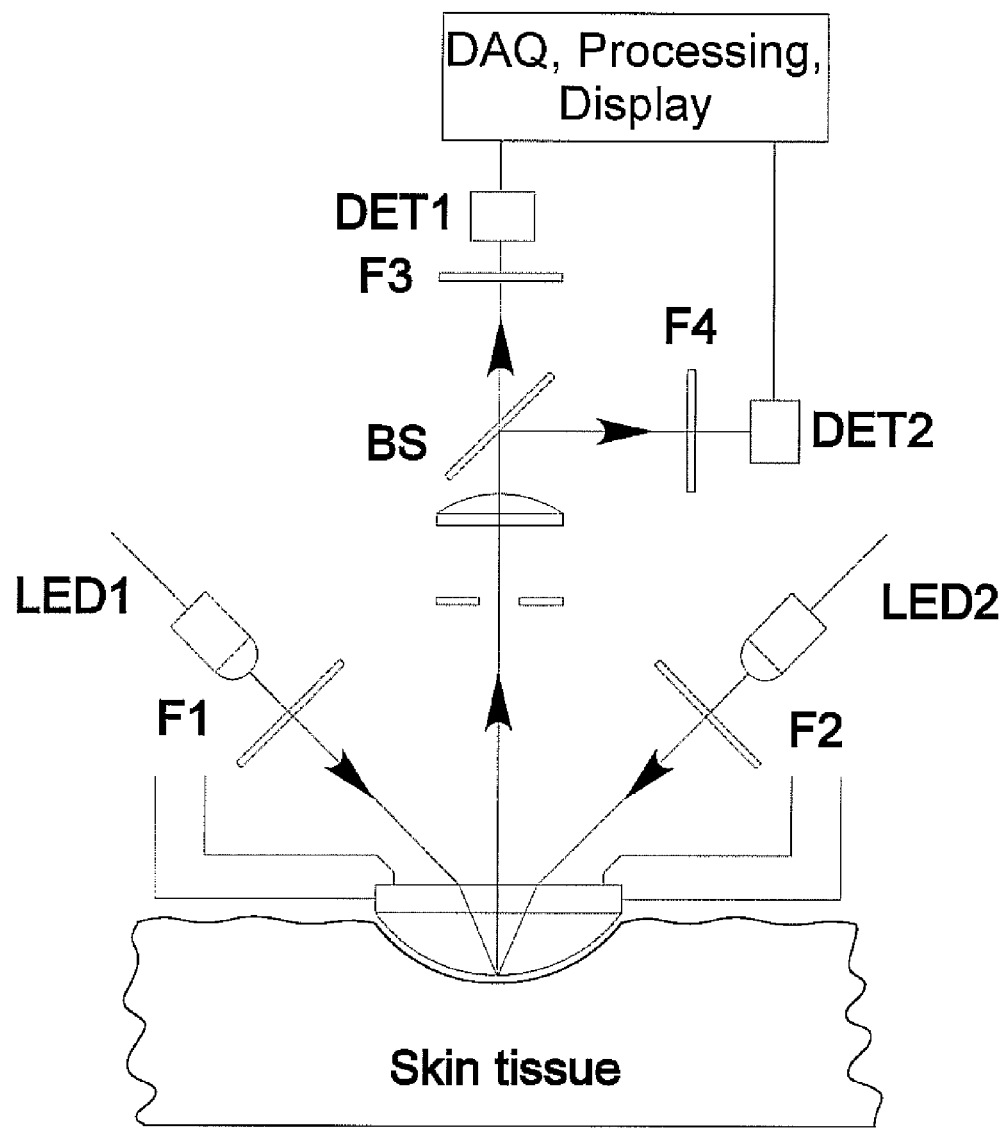
FIG. 14 shows the schematics of an alternative, simplified, reflectivity instrumentation setup.

FIG. 14 shows an alternative simplified reflectivity instrumentation setup, based on reflectivity measurements at two separate, strategically chosen wavelength positions. This setup replaces the "white" light source and multi-channel spectral detection described earlier with LED excitation at 480 and 620 nm, reflectivity measurements at these wavelengths, and thus significantly reduces the cost of the instrumentation needed to derive reflectivity based skin carotenoid levels.

REFERENCES

1. D. S. Michaud, D. D. Ffeskanich, E. B. Rimm, et al. "Intake of specific carotenoids and risk of lung cancer in 2 prospective US cohorts", Am. J. Clin. Nutr. 92, 990-997 (2000).
2. L. N. Kolonel, J. H. Hankin, A. S. Whittemore, et al., "Vegetables, fruits, legumes, and prostate cancer: a multiethnic case-control study"$_7$, Cancer Epidemiol. Biomarkers Prev. 9, 795-804 (2000).
3. S. Liu, J. E. Manson, I. M. Lee, et al., "Fruit and vegetable intake and risk of cardiovascular disease: the Women's Health Study", Am. J. Clin. Nutr. 72, 922-928 (2000).
4. Age-Related Eye Disease Study Group, "The relationship of dietary carotenoid and vitamin A, E, and C intake with age-related macular degeneration in case-control study", ARES Rep. No. 22, Arch. Opthalmol. (Chicago) 125, 1225-1232 (2007).
5. W. Gellermann, R. W. McClane, N. B. Katz, and P. S. Bernstein, "Method and Apparatus For Noninvasive Measurement Of Carotenoids And Related Chemical Substances in Biological Tissue", U.S. Pat. No. 6,205,354 B1 (March 2001).
6. T. R. Hata, T. A. Scholz, I. V. Ermakov, et al., "Noninvasive Raman spectroscopic detection of carotenoids in human skin", J. Invest. Dermatol. 115, 441-448 (2000).
7. I. V. Ermakov, M. R. Ermakova, R. W. McClane, W. Gellermann, "Resonance Raman Detection of Carotenoid Antioxidants in Living Human Tissues", Opt. Lett. 26, 1179-1181 (2001).
8. I. V. Ermakov, M. R. Ermakova, W. Gellermann, and J. Lademann, "Noninvasive selective detection of lycopene and beta-carotene in human skin using Raman spectroscopy", J. Biomed. Opt. 9, 332-338 (2004).
9. W. Gellermann, J. A. Zidichouski, C. R. Smidt, and P. S. Bernstein, "Raman detection of carotenoids in human tissue", in *Carotenoids and Retinoids: Molecular Aspects and Health Issues*, L. Packer, K. Kraemer, U. Obermueller-Jervic, and H. Sies, Eds., Chapter 6, pp. 86-114, AOCS Press, Champain, Ill. (2005).
10. S. Mayne et al., manuscript in preparation.
11. J. van de Kraats, D. van Norren, T T. J. M Berendschot, U.S. patent application US 2007/0252950.
12. W. Stahl, U. Heinrich, H. Jungmann, J. von Laar, M. Schietzel, H. Sies, and H. Tronnier, "Increased dermal carotenoid levels assessed by noninvasive reflection spectrophotometry correlate with serum levels in women ingesting betatene", J. Nutr. 128, 903 (1998).
13. W. Stahl, U. Heinrich, H. Jungmann, H. Tronnier, and H. Sies, "Carotenoids in Human Skin: Noninvasive Measurement and Identification of Dermal Carotenoids and Carotenol Esters", Methods in Enzymology 319, 494-502 (2000).
14. F. Niedorf, H. Jungmann, and M. Kietzmann, "Noninvasive reflection spectra provide quantitative information about the spatial distribution of skin chromophores", Med. Phys. 32, 1297-1307 (2005).
15. S. Alaluf, U. Heinrich, W. Stahl, H. Tronnier, and S. Wiseman, "Dietary Carotenoids Contribute to Normal Human Skin Color and UV Photosensitivity", J. of Nutrition 132, 399-403 (2002).

We claim:

1. A noninvasive method of measuring carotenoid levels in biological tissue, comprising the steps of:
    illuminating a localized region of tissue with light that overlaps the absorption bands of carotenoids in the blue wavelength region at or about 480 nm;
    illuminating the same region with light outside the carotenoid absorption band in the red wavelength region at or about 620 nm;
    applying pressure to the localized region for a predetermined period of time so as to reduce the level of blood chromophores in the localized region;
    using reflection spectroscopy to measure absorbances due to all chromophores remaining after pressurization in the blue and red wavelength regions; and
    determining the level of carotenoids in the localized region as the difference between the absorbances in the blue and red wavelength regions.

2. The method of claim 1, wherein the pressure is applied to the localized region of tissue for about 1 to 20 seconds.

3. The method of claim 1, further including the step of restricting blood flow to the localized region.

4. The method of claim 1, further including the step of:
    recording a dark spectrum $D(\lambda)$ providing a background signal intensity;
    measuring and storing a reflectivity standard; and
    wherein the reflectivity spectrum associated with the level of carotenoids in the localized region is calculated according to the expression:

$$R(\lambda) = \frac{T(\lambda) - D(\lambda)}{S(\lambda) - D(\lambda)} \cdot 100\%$$

where $R(\lambda)$ is a normalized reflectivity spectrum, and $T(\lambda)$, $S(\lambda)$ and $D(\lambda)$ are the intensity signals measured at wavelength $\lambda$ from the tissue and reflectivity standard, respectively, and $D(\lambda)$ is the signal at any wavelength $\lambda$ due to the dark spectrum intensity.

5. The method of claim 4, further including the step of converting the normalized reflectivity spectrum $R(\lambda)$ into an apparent optical density spectrum $A(\lambda)$ by taking the decimal logarithm for each spectral data point of the reflectivity spectrum, according to the relation:

$$A(\lambda) = -lg\left(\frac{R(\lambda)}{100}\right).$$

6. The method of claim 1, further including the step of comparing the level of carotenoids with normal biological tissue to assess the risk or presence of malignancy or other disease conditions.

7. The method of claim 1, wherein the tissue is human skin.

8. The method of claim 7, wherein the skin is on a fingertip or other portion of a hand.

9. A system for measuring carotenoid levels in biological tissue noninvasively, comprising:
    a source of light configured to illuminate a localized region of tissue with light that overlaps the absorption bands of carotenoids in the blue wavelength region at or about 480 nm;
    a source of light configured to illuminate the same localized region of tissue with light outside the carotenoid absorption band in the red wavelength region at or about 620 nm;
    a pressurization device configured to apply pressure to the localized region for a predetermined period of time so as to reduce the level of blood chromophores in the localized region;
    a spectrograph configured to measure absorbances due to all chromophores remaining after pressurization in the blue and red wavelength regions; and
    a processor configured to determine the level of carotenoids in the localized region as the difference between the absorbances in the blue and red wavelength regions.

10. The system of claim 9, wherein the pressure is applied to the tissue for about 1 to 20 seconds.

11. The system of claim 9, wherein the device for applying pressure is an optically transparent element through which the light and reflection spectra pass.

12. The system of claim 9, wherein the device for applying pressure is a lens through which the light and reflection spectra pass.

13. The system of claim 9, further including a cuff or other device for restricting blood flow to the localized region.

14. The system of claim 9, wherein the light sources are derived from a single white light source substantially spanning the spectral range from about 350 to 900 nm.

15. The system of claim 9, wherein the light sources are separate sources, one at or about 480 nm and the other at or about 620 nm.

16. The system of claim 9, wherein:
    the device for applying pressure to the localized region for a predetermined period of time is contained in a probe body;
    light from the source is delivered to the probe through a first optical fiber; and
    reflectance spectra is carried from the probe body to the spectrograph through a second optical fiber.

* * * * *